United States Patent
Sato

(10) Patent No.: US 6,810,106 B2
(45) Date of Patent: Oct. 26, 2004

(54) X-RAY FLUORESCENCE THICKNESS MEASUREMENT DEVICE

(75) Inventor: Masao Sato, Chiba (JP)

(73) Assignee: SII NanoTechnology Inc., Chiba (JP)

(*) Notice: Subject to any disclaimer, the term of this patent is extended or adjusted under 35 U.S.C. 154(b) by 260 days.

(21) Appl. No.: 09/916,519

(22) Filed: Jul. 27, 2001

(65) Prior Publication Data

US 2002/0012418 A1 Jan. 31, 2002

(51) Int. Cl.[7] .............................................. G01B 15/02
(52) U.S. Cl. ........................................ 378/50; 378/44
(58) Field of Search ............................. 378/44–50, 43, 378/147–148

(56) References Cited

U.S. PATENT DOCUMENTS 3,806,726 A * 4/1974 Ishijima ...................... 378/49
6,038,280 A * 3/2000 Rossiger et al. .............. 378/50

* cited by examiner

*Primary Examiner*—Edward J. Glick
*Assistant Examiner*—Hoon Song
(74) *Attorney, Agent, or Firm*—Adams & Wilks

(57) ABSTRACT

An X-ray fluorescence film thickness measuring device has an X-ray generating system generating and irradiating primary X-rays. A focusing system focuses primary X-rays irradiated from the X-ray generating system onto microscopic measurement regions in a sample. A sample observation optical system is used to observe the sample during focusing of the primary X-rays for use in positioning of the microscopic measurement regions relative to the primary X-rays. A first sensor with low counting efficiency but high energy resolution detects X-ray fluorescence generated from a sample having the microscopic measurement regions. A second sensor has low energy resolution but high counting efficiency compared to the first sensor. Each of a pair of pre-amplifiers receives a signal from a respective one of the first and second sensors.

26 Claims, 8 Drawing Sheets

PRIOR ART    FIG. 5

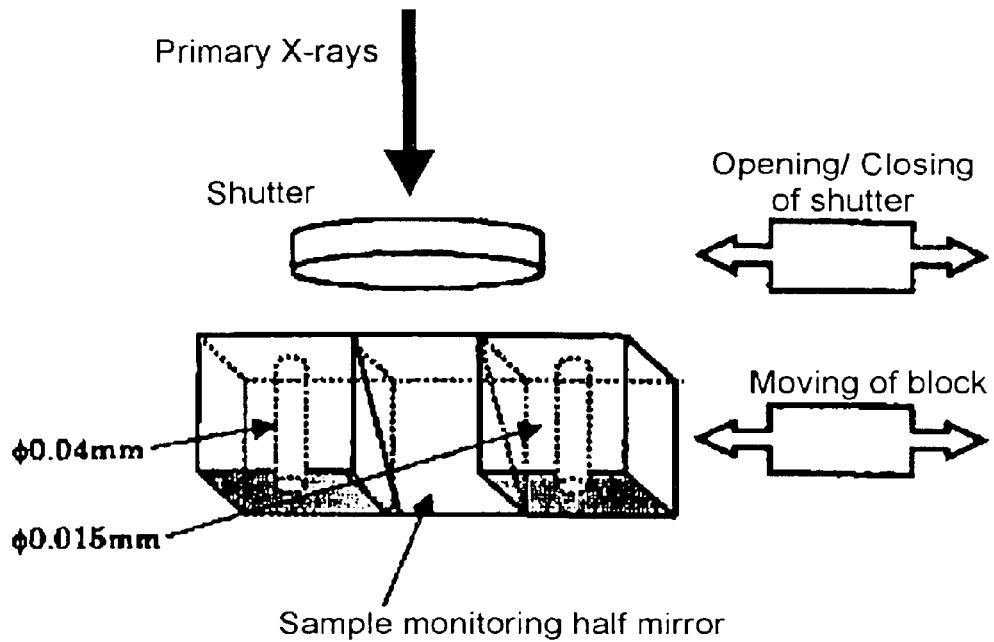
FIG. 7A _PRIOR ART_
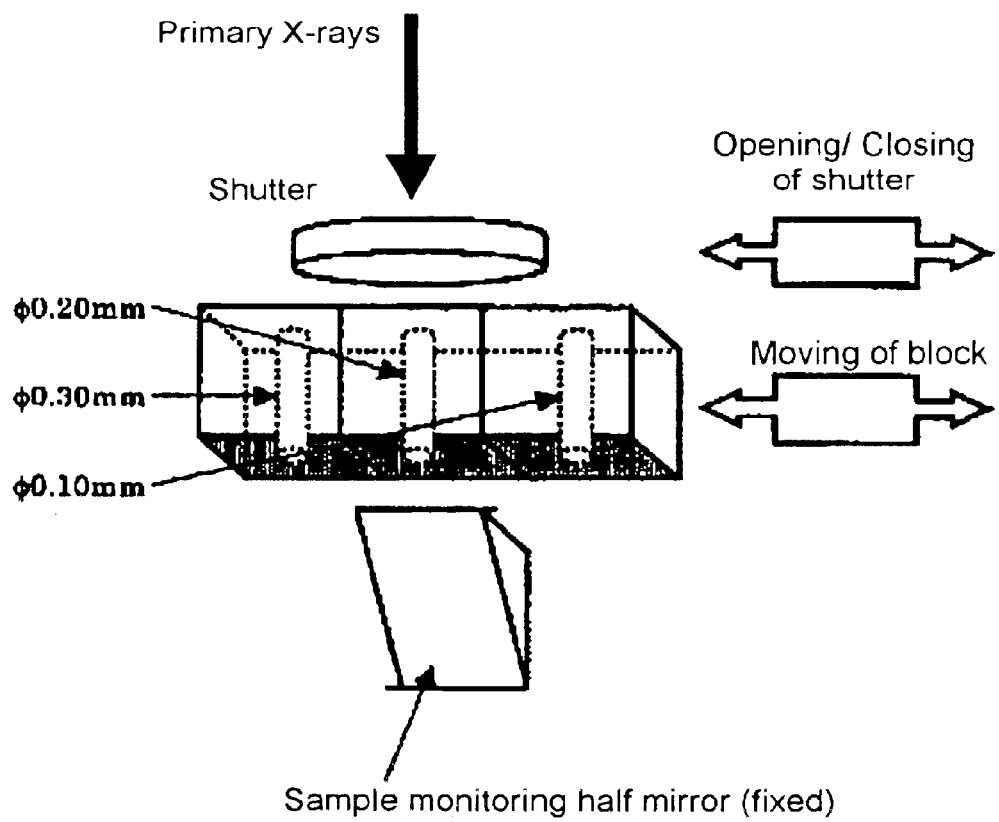
FIG. 7B _PRIOR ART_

X-RAY FLUORESCENCE THICKNESS MEASUREMENT DEVICE

BACKGROUND OF THE INVENTION

1. Field of the Invention

The present invention relates to an energy dispersion type fluorescent X-ray type thickness measurement device having the merits of being both multi-elemental and non-destructive and being for use in film thickness management in the surface processing industry such as the plating and sputtering of films.

2. Background Information

In the related art, the film composition in surface processing is already known, so energy dispersion type fluorescent X-ray film thickness measurement devices are utilized in production lines with the purpose of quality management, which incurs the limitation that it is difficult to increase measuring time This means that a higher count rate is required using the energy resolution, which means utilizing mainly fluorescent X-ray film thickness measurement devices utilizing proportional counting tubes. However, in the case of utilization in research and development, accuracy and sensitivity are more important than putting restraints on measuring time. For this purpose, fluorescent X-ray film measurement devices mounted with Si (Li) semiconductor detectors or PIN diode detectors have been utilized because they demonstrate superior energy resolution.

FIG. 5 shows an example of a related art fluorescent X-ray film thickness measuring device. A high voltage is applied from an X-ray generation high voltage source 1. Primary X-ray 3 emitted from an X-ray tube 2 are then irradiated onto a sample 5 by means 4 for focusing onto a microscopic unit using a slit, collimator, or capillary utilizing a total reflection phenomena. A sample observation mirror 6 and a sample observation optical system 7 are provided for positioning of the measurement locations by movement of the sample 5 through control of a stage 19 by a control and computing section 17. Fluorescent X-rays 8 generated by the sample are detected by an energy dispersion-type sensor 9. A pre-amplifier 10 is provided to receive an output of the sensor 9. A pre-amplifier 10 is provided to receive an output of the sensor 9 and a linear amplifier 11 receives the output of the pre-amplifier, which is supplied to a frequency analyzer (MCA) 12 with an output signal thereof being quantitatively processed by a control and computing section 17.

Further, a recent tendency is to employ microscopic parts in surface processing units. This means providing collimators for converging and irradiating X-rays and an optical sample monitoring system for confirming where X-rays are being irradiated from. FIG. 7A and FIG. 7B show examples of two different types of sample irradiating systems of the related art. In FIG. 7A, a half mirror and a collimator block are located at the same height in such a manner that an X-ray irradiation axis and an optical sample monitoring axis coincide. In FIG. 7B, a half mirror is located below the collimator block.

The energy dispersion detector has a detection performance whereby the resolution and the count rate conflict with each other. Typically, when the device thickness and surface area of the sensor are increased in order to increase the count rate, the resolution either deteriorates or does not function at all.

Conventionally, a proportional counter tube is typically employed when carrying out film thickness measurements on thin films using a fluorescent X-ray film thickness measurement device. Accurate film thickness and composition measurements are possible without performing special processing providing that the atomic numbers of the elements making up the thin film and materials (substrate) are separable to a certain extent when using a proportional counter tube. However, when the atomic numbers are separated into the neighboring nickel (Z=28) and zinc (Z=29), there is a problem that the peaks to be counted overlap with each other, which needs to be remedied. For example, there is a secondary filtering method whereby a thin plate of cobalt (Z=27) is inserted prior to detection and peak separation is achieved by utilizing the difference in results for absorption of copper, and a digital filtering method which provides peak separation by performing numerical operation on the shapes of the peaks. The secondary filtering is limited to appropriate combinations. This is therefore effective in the case of dedicated function but is not appropriate in cases where the object is to take measurements for various combinations. The digital filtering method is capable of being applied to various combinations but there are problems with stability compared with secondary filtering methods that accompany peak separation errors.

If peak separation is demanded, it is possible to use an Si (Li) semiconductor detector with superior energy resolution. However, when an Si (Li) semiconductor detector is utilized, it is necessary to periodically supply liquid nitrogen as a coolant, which causes problems with respect to both costs and operation. PIN diode detectors that employ Peltier cooling are therefore adopted to resolve this problem of supplying liquid nitrogen, but this causes a substantial deterioration in the energy resolution. This is, however, limited to low energy X-ray applications due to the detection rate in principle being poor with respect to high-energy X-rays.

Moreover, optical sample monitoring systems have the following problems.

FIG. 8 shows a conceptual view of broadening of an X-ray irradiation beam when a collimator is used. As shown in FIG. 8, when a distance L1 from the end of the collimator to the sample is made long, there is substantial broadening of the X-ray beam, and it is therefore necessary to shorten the length L1 in order to implement a microscopic beam.

With an optical sample monitoring system, with the method of locating the half mirror below the collimator block shown in FIG. 7B, the distance between the device body consisting of the collimator block and the mirror, and the sample, is made long and it is ensured that the sample does not come into contact with the device body. However, when this distance is made long, the actual dimensions of the irradiation also become large. This means that broadening is substantial even if a small collimator is prepared, which makes implementation of a microscopic beam difficult. As shown in FIG. 7A, when the purpose is to implement a microscopic beam, a half mirror is located at the position of the collimator block, a still image display saved prior to taking measurements is taken when measurements are to be taken, and the distance between the sample and the collimator is made small. As the purpose of taking measurements with a microscopic portion is on the whole materials which do not have projections, such as wafers, there is no chance of damage being incurred by the device body through contact with the sample even if the distance between the sample and the collimator is small.

However, as cases of measuring vehicle parts and electronic components etc. which have projections with a normal beam size are common, it is preferable to obtain a real image of the location currently being measured rather than having a still image. This causes inconveniences with the collimator block of the structure shown in FIG. 7A. In order to resolve the above situation, the present invention sets out to tackle the problem of measuring a broad range of materials in a manner compatible with low energy to high energy fluorescent X-rays.

SUMMARY OF THE INVENTION

According to the present invention, counting is performed simultaneously using a two system X-ray detector by dividing the energy regions in such manner that a PIN diode detector of superior energy resolution is utilized for low energy regions where X-ray energies are close to each other and a proportional counter tube or CdZnTe detector with a superior count rate but with poor resolution for high energy regions is utilized when the count rate is poor using the PIN diode detector high resolution is not required.

Further, the distance is made short between the collimator and the sample when a microscopic beam is utilized. A half mirror is positioned at the same height as the collimator at a side surface of the collimator. The position is then decided upon using the half mirror. Movement in a horizontal direction is then performed so that a prescribed collimator approaches and irradiation using a microscopic beam then takes place, with a still image taken prior to taking measurements being displayed during measurement. When a normal beam is utilized, a second collimator block is provided above the half mirror, with a real image provided by the half mirror then being visible during measurement.

BRIEF DESCRIPTION OF THE DRAWINGS

FIG. 7A is a perspective view of a related normal sub-millimeter collimator.

FIG. 7B is a perspective view of a related collimator of microscopic dimensions.

DETAILED DESCRIPTION OF THE PREFERRED EMBODIMENTS

Figure 1:
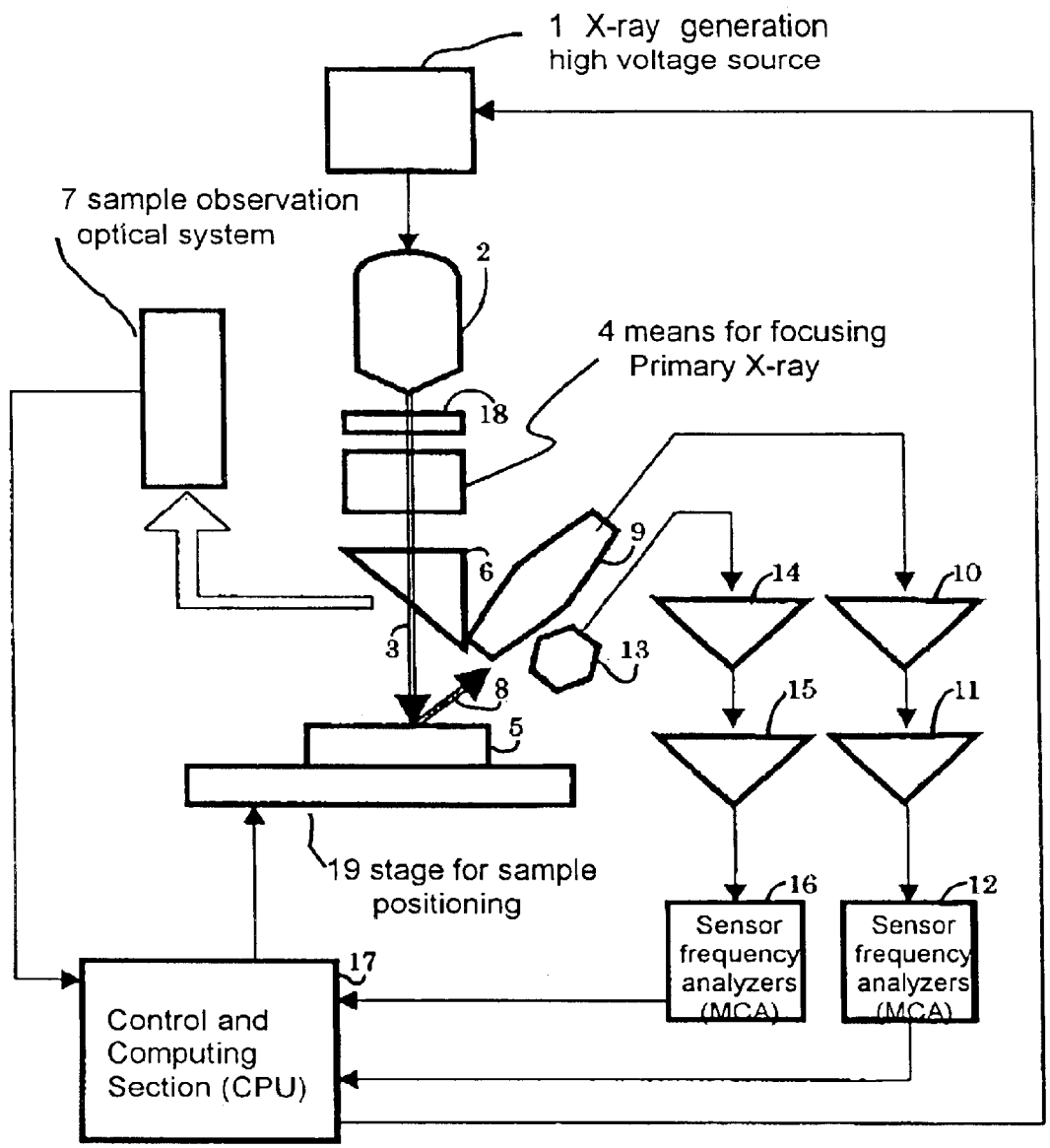
FIG. 1 is block diagram showing a first embodiment of the present invention.

FIG. 1 shows an example of an embodiment of an energy dispersion type fluorescent X-ray film thickness measuring device.

A high voltage is applied from an X-ray generation high voltage source 1. Primary X-rays 3 emitted from an X-ray tube 2 are then irradiated onto a sample 5 by means 4 for focusing onto a microscopic unit using a slit, collimator, or capillary utilizing a total reflection phenomena.

At the time of irradiation, since measurement regions are microscopic, a sample observation mirror 6 and a sample observation optical system 7 are provided for positioning of the measurement locations by movement of the sample 5 through control of a stage 19 by a control and computing section 17. Fluorescent X-rays 8 generated by the sample are positioned in such a manner as to be detected by an energy dispersion-type first sensor 9 and a second sensor 13. A sensor 13 characterized by high resolution, for example a PIN diode detector or a high resolution X-ray detector such as a silicon drift chamber, is provided at an energy dispersion-type X-ray detector. When a PIN diode detector is utilized in the sensor 13, resolution (FWHM) with respect to the Mn-Ka line (5.9 keV) is in the order of 200 eV, and the count rate is in the order of a few tens of thousands cps. However, this is used as a low energy detector due to the detection rate for high energy X-rays being poor. When a proportional counter tube is used as the sensor 9, the resolution is in the order of 1 keV and the count rate can be in the order of a few tens of thousands of cps. When a scintillation counter is used, the resolution is poor at a few keV, but a count rate of a few hundred thousand cps is possible.

In the high energy region, since there is less overlapping of X-rays there is no need for resolution and high energy detection efficiency is also good, which means that it acts as a high energy detector. In the case of adopting a CdZnTe detector, since it has the same probe shape as the PIN diode detector it has the advantage that it can be arranged without being subject to space limitations.

Figure 2:
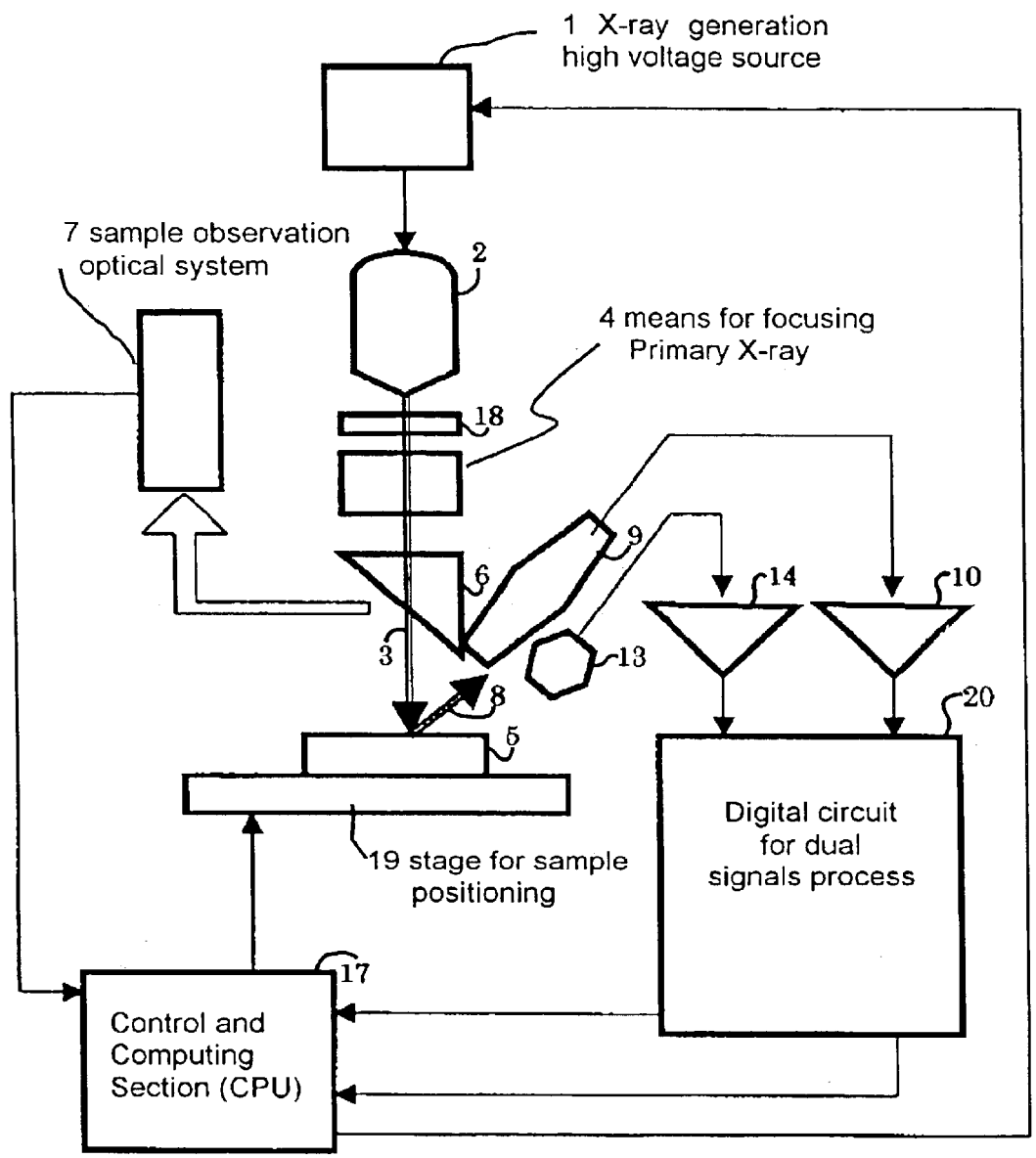
FIG. 2 is block diagram showing a second embodiment of the present invention.

In the embodiment shown in FIG. 1, stages after pre-amplifiers 10 and 14 of each detector (sensors 9 and 13) are made up of respective linear amplifiers 11 and 15, and frequency analyzers (MCA) 12 and 16, with respective signals being quantitatively processed by a common control and computing section 17. As shown in FIG. 2, it is also possible for the stage following the pre-amplifiers 10 and 14 of each detector (sensors 9 and 13) to be taken as a single digital circuit 20.

Figure 3:
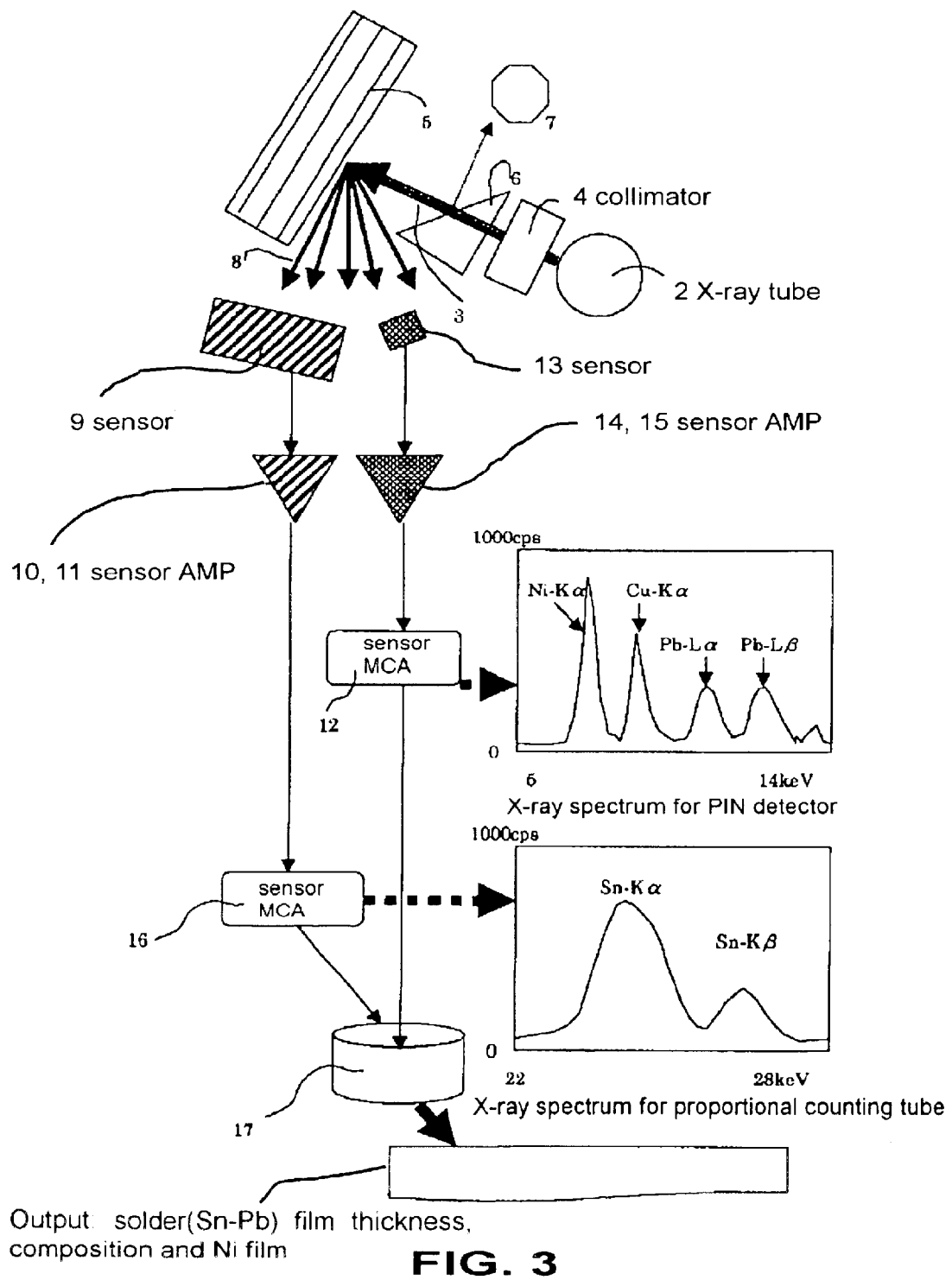
FIG. 3 is a view showing an example of two system spectral measuring for sensors of this embodiment.

With the embodiment in FIG. 3, an example is shown of an X-ray spectrum of a PIN diode detector counting an X-ray spectrum for an Ni-Ka line (7.47 keV), a Cu-Xa line (8.04 keV) and a Pb-La line (10.55 keV) using a sensor 13 and counting an Sn-Ka line (25.19 keV) using a sensor 9 for the case where the sample 5 is solder plating on nickel plating on copper, and an example is shown of an X-ray spectrum for a proportional counter tube.

Figure 4:
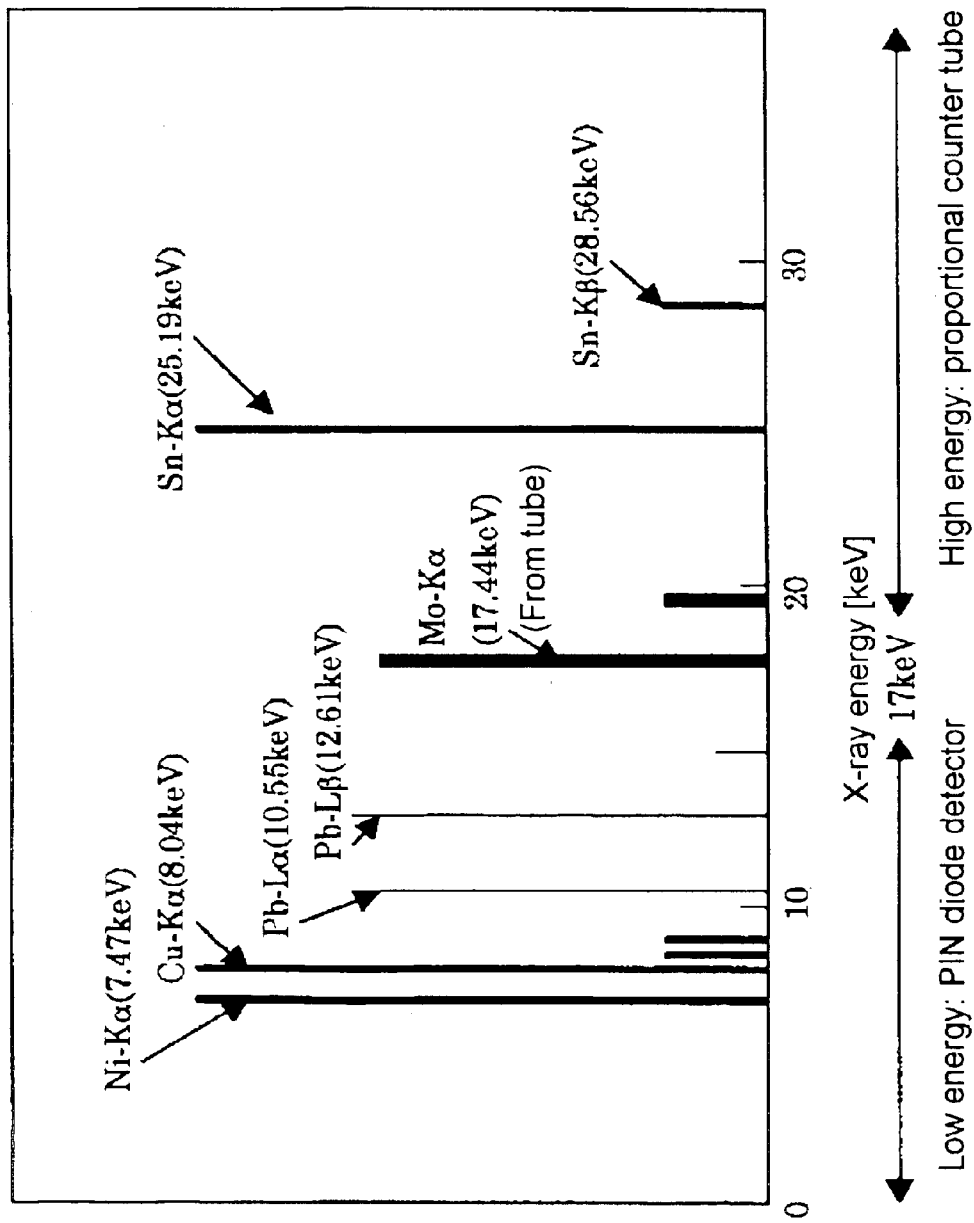
FIG. 4 is a view showing X-ray energy relationships and counting ranges for each detector.
Figure 5:
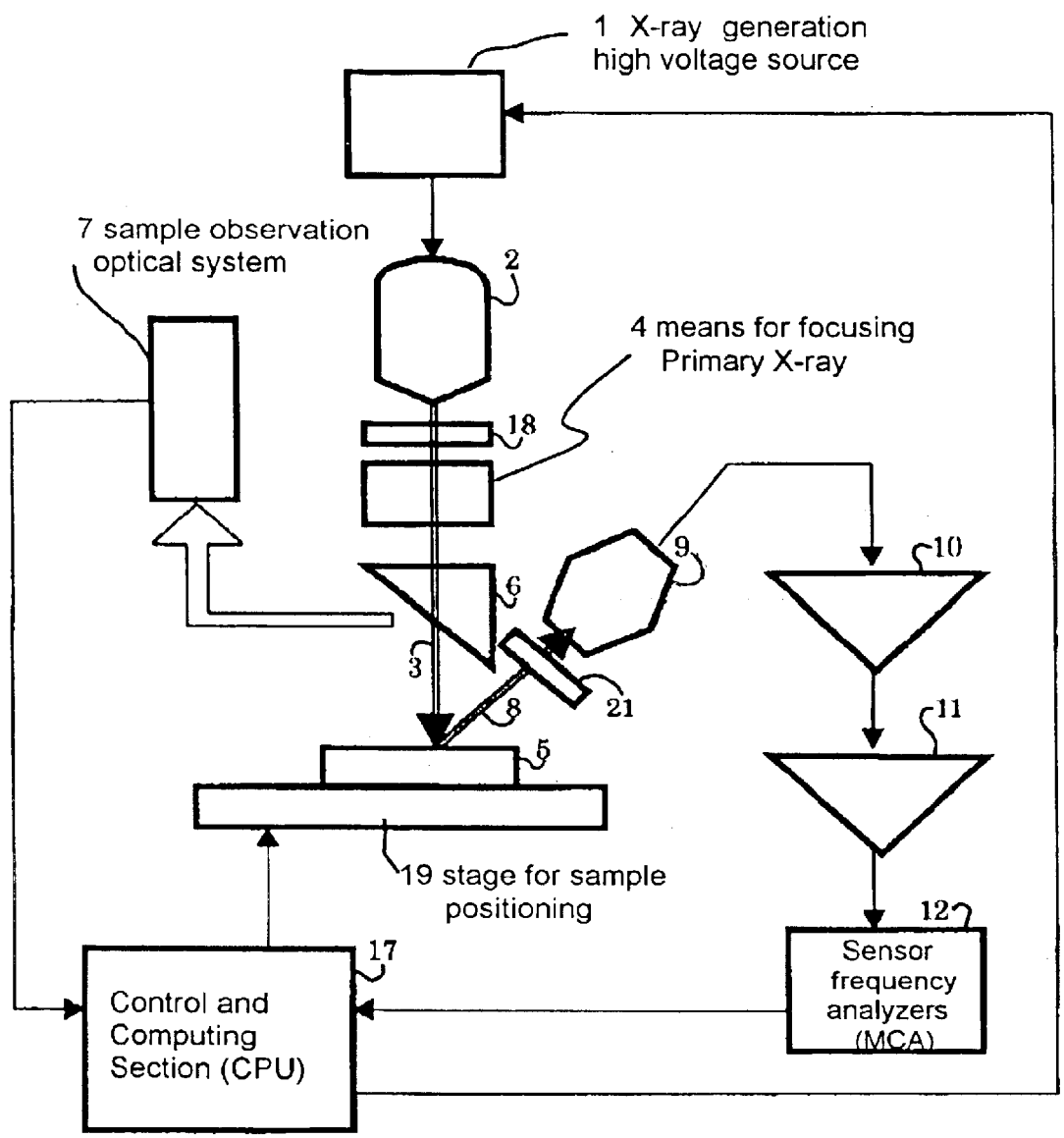
FIG. 5 is a block diagram showing a related energy dispersion type fluorescent X-ray film thickness counter.

With regards to allotting detection energy regions to each of the detectors (sensors 9 and 13), as shown in FIG. 4, a system is adopted in this embodiment where, for example, a molybdenum target is utilized at the X-ray tube 2, and a PIN diode detector is therefore utilized for low energy regions of 17 keV or less taking the Mo-Ka line (17.44 keV) as a standard, and a proportional counter tube is utilized for high energy regions exceeding 17 keV. Other characteristic X-ray energies are then set as boundary when other targets are used. When a CdZnTe detector is utilized as a high-energy detector 9, a more compact system can be constructed as a result of the shape being small.

Figure 6:
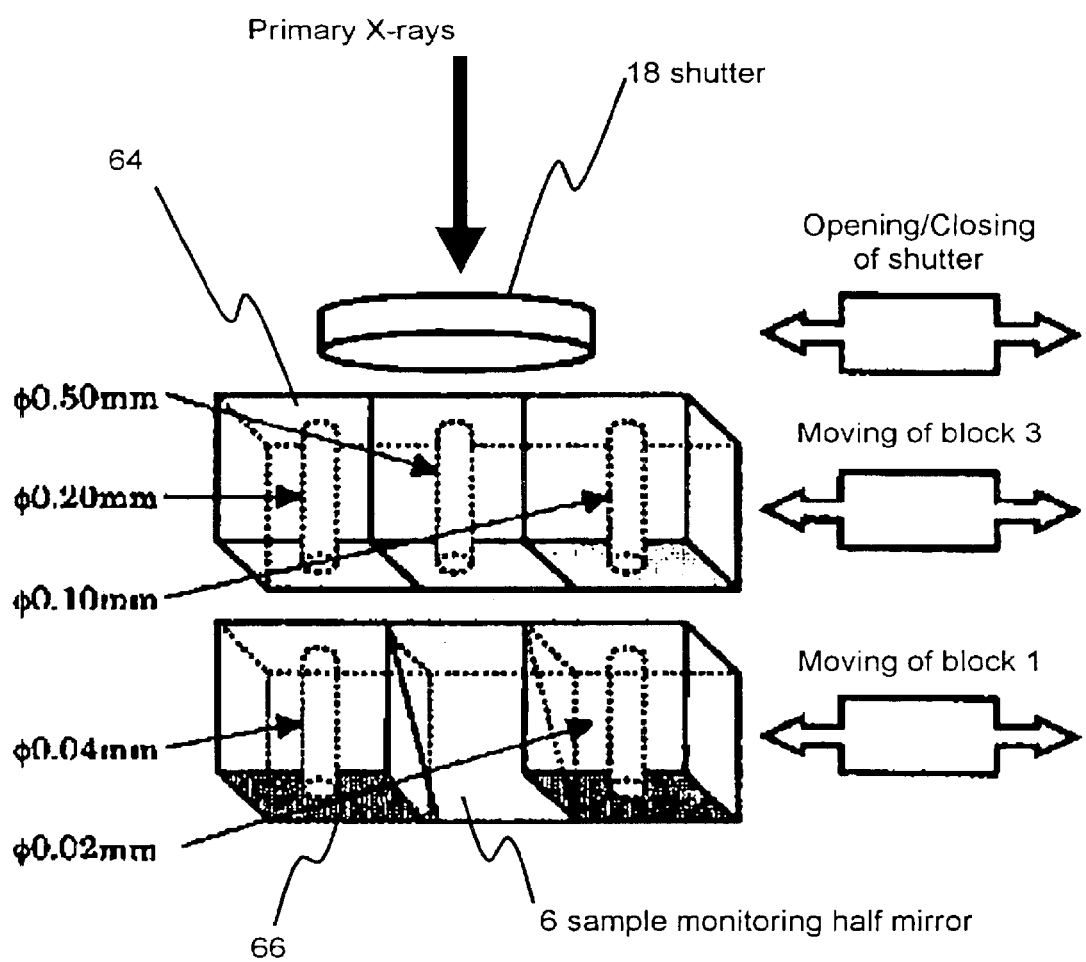
FIG. 6 is a perspective view showing an optical sample monitoring system of the present invention.

FIG. 6 shows an embodiment of a sample irradiating system of the present invention. Blocks 64 and 66 are provided so as to be moveable in a direction orthogonal with respect to the primary X-rays, and an arbitrary collimator unit or the half mirror 6 can be located so as to be positioned on the optical axis of the X-rays. In FIG. 6, when a shutter 18 is set to be closed while using a microscopic collimator (where block 66 is, for example, 0.02 mm or 0.24 mm), block 66 monitors the sample at the position of the mirror 6 of FIG. 1.

The block 64 is located at the position of the means 4 for focusing the primary X-rays in FIG. 1. The block 64 is set to a central position (open to a sufficient large extent, for example, 0.50 mm, to ensure that the primary X-rays do not block the lower collimator) using a signal to commence measuring using the block, the block 66 is set to a prescribed collimator position (for example, 0.02 mm or 0.04 mm), and the shutter 2 is set to be open.

Figure 8:
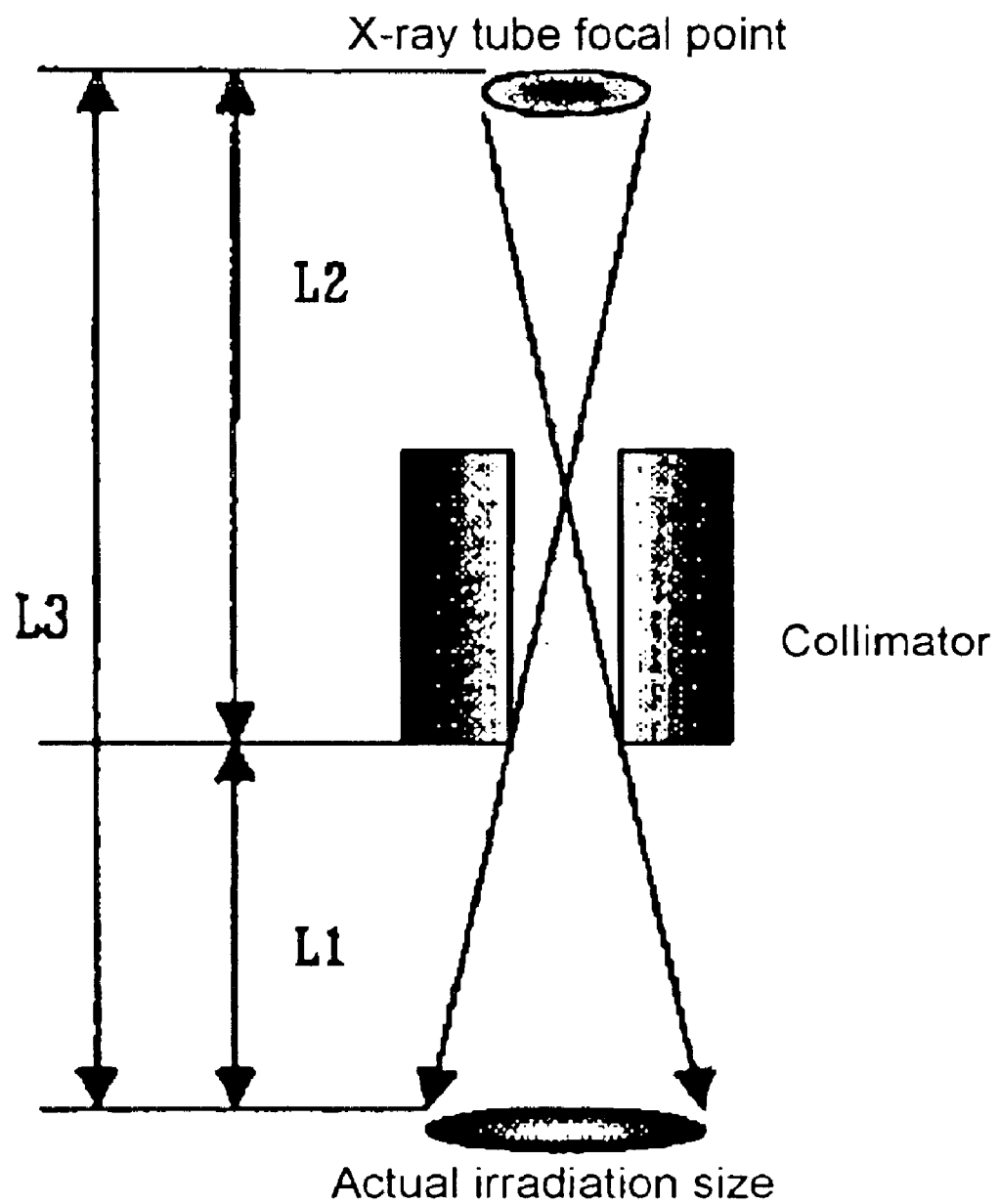
FIG. 8 is a conceptual view of broadening of an X-ray irradiation beam when a collimator is used.

A still image taken when the shutter 18 is closed is shown during measuring. FIG. 8 shows a conceptual view of broadening of an X-ray irradiation beam when a collimator is used. It can be understood that broadening is slight if the distance L1 from the end of the collimator to the sample is short. It can be seen that broadening is effectively repressed when the distance from the structure of the sample and the mirror 6, i.e. the reference focal point, is 10 mm, but this is particularly noticeable with a still shorter focal point of 2 mm.

When a normal collimator is used (for example, a 0.10 mm or 0.20 mm collimator), the block 66 is set to the position of the mirror 6 and the sample is monitored regardless of whether the shutter 2 is open or closed. The block 64 is set to a prescribed collimator position using a measurement start signal, the block 66 is fixed at the location of the mirror 6, and the shutter 2 is opened. A sample image is also shown at once during measuring. In this case beam broadening is not a problem because the collimator size is large to begin with and sample scanning is possible immediately.

The present invention enables efficient and accurate thin film measurement from low energy to high energy using X-ray fluorescence, at high resolution, without the need for high sensitivity, or liquid nitrogen.

In the present invention, a system is realized where microscopic beams of a few tens of microns can be realized for materials where the measuring region is microscopic, and where a normal beam of sub-millimeter level is used for materials where this is not the case, with confirmation then being possible using a real image.

It is the object of the present invention to provide a versatile fluorescent X-ray film thickness measuring device capable of being compatible with the composition or shape of target materials or with performance required in measurements.

What is claimed is:

1. An X-ray fluorescence film thickness measuring device comprising:

an X-ray generating system having a high-voltage power source and an X-ray tube for irradiating primary X-rays;

focusing means for focusing primary X-rays irradiated from the X-ray generating system onto microscopic measurement regions in a sample using a slit unit, a collimator, or a capillary unit utilizing a total reflection phenomenon;

a sample observation optical system for observing the sample during focusing of the primary X-rays for use in positioning of the microscopic measurement regions relative to the primary X-rays;

a system having a liquid nitrogen-less PIN diode X-ray detector or a silicon drift chamber used as a first sensor with low counting efficiency but high energy resolution for detecting X-ray fluorescence generated from the sample, and a proportional counter, CdZnTe detector, or a scintillation counter as a second sensor having low energy resolution but high counting efficiency compared to the first sensor, the first and second sensors being arranged side-by-side in a sample chamber that is open to the atmosphere and not evacuated, and the system being divided between the first and second sensors according to energy of X-ray fluorescence by utilizing the first sensor for X-ray fluorescence from low energy and utilizing the second sensor for X-ray fluorescence from high energy;

a pair of pre-amplifiers each for receiving a signal from a respective one of the first and second sensors;

a pair of linear amplifiers each for receiving a signal from a respective one of the pre-amplifiers;

a pair of frequency analyzers each for analyzing a frequency signal from a respective one of the linear amplifiers; and common control and computing sections for quantitatively processing signals from the frequency analyzers.

2. An X-ray fluorescence film thickness measuring device comprising:

an X-ray generating system having a high-voltage power source and an X-ray tube for irradiating primary X-rays;

focusing means for focusing primary X-rays irradiated from the X-ray generating system onto microscopic measurement regions in a sample using a slit unit, a collimator, or a capillary unit utilizing a total reflection phenomenon;

a sample observation optical system for observing the sample during focusing of the primary X-rays for use in positioning of the microscopic measurement regions relative to the primary X-rays;

a system having a liquid nitrogen-less PIN diode X-ray detector or a silicon drift chamber used as a first sensor with low counting efficiency but high energy resolution for detecting X-ray fluorescence generated from the sample, and a proportional counter, CdZnTe detector, or a scintillation counter as a second sensor having low energy resolution but high counting efficiency compared to the first sensor, the first and second sensors being arranged side-by-side in a sample chamber that is open to the atmosphere and not evacuated, and the system being divided between the first and second sensors according to energy of X-ray fluorescence by utilizing the first sensor for X-ray fluorescence from low energy and utilizing the second sensor for X-ray fluorescence from high energy;

a pair of pre-amplifiers each for receiving a signal from a respective one of the first and second sensors;

a single digital circuit for amplifying and analyzing frequencies of signals from the pre-amplifiers; and common control and computing sections for quantitatively processing signals from the single digital circuit.

3. A fluorescent X-ray film thickness measuring device comprising:

an X-ray generating system having a high-voltage power source and an X-ray tube for generating and emitting primary X-rays;

focusing means including a first collimator block for focusing the primary X-rays onto microscopic measurement regions in a sample and a second collimator block disposed above the first collimator block for receiving primary X-rays from the X-ray generating system and focusing the primary X-rays toward the first collimator block;

a sample observation optical system for observing the sample during focusing of the primary X-rays for use in positioning of the microscopic measurement regions relative to the primary X-rays;

a detector for detecting X-ray fluorescence generated from the sample;

a pre-amplifier for amplifying a signal from the detector;

a linear amplifier for amplifying a signal from the pre-amplifier; and a frequency analyzer for analyzing a frequency of a signal from the linear amplifier.

4. A fluorescent X-ray film thickness measuring device according to claim 3; wherein the first collimator block comprises a half mirror section and a collimator section located at a side surface of the half mirror section, and the second collimator block comprises a plurality of collimator units located in order along a lateral direction, the first collimator block and the second collimator block being movable in a direction generally perpendicular to an optical axis of the primary X-rays; and further comprising an arbitrary collimator section or half mirror section disposed at a position along an optical axis of the first and second collimator blocks.

5. An X-ray fluorescence film thickness measuring device comprising:

an X-ray generating system for generating and irradiating primary X-rays;

focusing means for focusing primary X-rays irradiated from the X-ray generating system onto microscopic measurement regions in a sample;

a sample observation optical system for observing the sample during focusing of the primary X-rays for use in positioning of the microscopic measurement regions relative to the primary X-rays;

a first sensor with low counting efficiency but high energy resolution for detecting X-ray fluorescence generated from the sample;

a second sensor having low energy resolution but high counting efficiency compared to the first sensor; and a pair of pre-amplifiers each for receiving a signal from a respective one of the first and second sensors.

6. An X-ray fluorescence film thickness measuring device according to claim 5; wherein the focusing means comprises a slit unit.

7. An X-ray fluorescence film thickness measuring device according to claim 5; wherein the focusing means comprises a collimator.

8. An X-ray fluorescence film thickness measuring device according to claim 5; wherein the focusing means comprises a capillary unit utilizing a total reflection phenomenon.

9. An X-ray fluorescence film thickness measuring device according to claim 5; wherein the first sensor comprises a liquid nitrogen-less PIN diode X-ray detector.

10. An X-ray fluorescence film thickness measuring device according to claim 5; wherein the first sensor comprises a silicon drift chamber.

11. An X-ray fluorescence film thickness measuring device according to claim 5; wherein the second sensor comprises a proportional counter.

12. An X-ray fluorescence film thickness measuring device according to claim 5; wherein the second sensor comprises a CdZnTe detector.

13. An X-ray fluorescence film thickness measuring device according to claim 5; wherein the second sensor comprises a scintillation counter.

14. An X-ray fluorescence film thickness measuring device according to claim 5; wherein the first and second sensors are arranged side-by-side in a sample chamber that is open to the atmosphere and not evacuated.

15. An X-ray fluorescence film thickness measuring device according to claim 5; further comprising a pair of linear amplifiers each for amplifying a signal from a respective one of the pre-amplifiers; and a pair of frequency analyzers each for analyzing a frequency of the signal from a respective one of the linear amplifiers.

16. An X-ray fluorescence film thickness measuring device according to claim 15; further comprising common control and computing sections for quantitatively processing signals from the frequency analyzers.

17. An X-ray fluorescence film thickness measuring device according to claim 5; further comprising a digital circuit for amplifying and analyzing frequencies of signals from the pre-amplifiers.

18. An X-ray fluorescence film thickness measuring device according to claim 5; further comprising common control and computing sections for quantitatively processing signals from the single digital circuit.

19. An X-ray fluorescence film thickness measuring device according to claim 5; wherein the focusing means comprises a first collimator block for focusing the primary X-rays onto the microscopic measurement regions and a second collimator block disposed above the first collimator block for receiving primary X-rays from the X-ray generating system and irradiating the primary X-rays toward the first collimator block.

20. An X-ray fluorescence film thickness measuring device according to claim 19; wherein the first collimator block comprises a half mirror section and a collimator section disposed at a side surface of the half mirror section; and wherein the second collimator block comprises a plurality of collimator units, the first collimator block and the second collimator block being movable in a direction generally perpendicular to an optical axis of the primary X-rays.

21. An X-ray fluorescence film thickness measuring device according to claim 20; further comprising another collimator section or half mirror section disposed at a position along an optical axis of the first and second collimator blocks.

22. A fluorescent X-ray film thickness measuring device comprising:

an X-ray generating system for generating and emitting primary X-rays;

a first collimator block for focusing the primary X-rays onto microscopic measurement regions in a sample;

a second collimator block disposed above the first collimator block for receiving primary X-rays from the X-ray generating system and focusing the primary X-rays toward the first collimator block;

a sample observation optical system for observing the sample during focusing of the primary X-rays for use in positioning of the microscopic measurement regions relative to the primary X-rays;

a detector for detecting X-ray fluorescence generated from the sample;

a pre-amplifier for amplifying a signal from the detector;

a linear amplifier for amplifying a signal from the pre-amplifier; and a frequency analyzer for analyzing a frequency of a signal from the linear amplifier.

23. A fluorescent X-ray film thickness measuring device according to claim 22; wherein the first collimator block comprises a half mirror section and a collimator section disposed at a side surface of the half mirror section.

24. A fluorescent X-ray film thickness measuring device according to claim 23; wherein the second collimator block comprises a plurality of collimator units.

25. A fluorescent X-ray film thickness measuring device according to claim 24; further comprising another collimator section or half mirror section disposed at a position along an optical axis of the first and second collimator blocks.

26. A fluorescent X-ray film thickness measuring device according to claim 22; wherein the detector comprises a first sensor with low counting efficiency but high energy resolution for detecting X-ray fluorescence generated from the sample and a second sensor having low energy resolution but high counting efficiency compared to the first sensor.

* * * * *